(12) United States Patent
Bush

(10) Patent No.: US 11,873,271 B1
(45) Date of Patent: Jan. 16, 2024

(54) GLYCERIN SEPARATION SYSTEM AND METHOD OF USE

(71) Applicant: Donald Lee Bush, Texarkana, TX (US)

(72) Inventor: Donald Lee Bush, Texarkana, TX (US)

( * ) Notice: Subject to any disclaimer, the term of this patent is extended or adjusted under 35 U.S.C. 154(b) by 0 days.

(21) Appl. No.: 16/428,214

(22) Filed: May 31, 2019

Related U.S. Application Data

(60) Provisional application No. 62/678,515, filed on May 31, 2018.

(51) Int. Cl.
| | | |
|---|---|---|
| *C07C 29/76* | (2006.01) | |
| *B01D 21/00* | (2006.01) | |
| *B01D 21/32* | (2006.01) | |

(52) U.S. Cl.
CPC ............ *C07C 29/76* (2013.01); *B01D 21/009* (2013.01); *B01D 21/0024* (2013.01); *B01D 21/32* (2013.01)

(58) Field of Classification Search
CPC .......... C07C 29/76; B01D 21/00; B01D 21/32
See application file for complete search history.

(56) References Cited

U.S. PATENT DOCUMENTS

| | | | |
|---|---|---|---|
| 6,603,048 B1 * | 8/2003 | Corbin ..................... | B01J 20/18 568/870 |
| 7,871,448 B2 * | 1/2011 | Jackam ................... | C10L 1/026 554/167 |
| 9,174,902 B2 * | 11/2015 | Soper ....................... | C07C 29/80 |
| 9,868,682 B2 * | 1/2018 | Ko ........................... | C07C 29/76 |
| 10,836,695 B2 * | 11/2020 | Freeman ................ | B01J 19/245 |
| 10,953,347 B2 * | 3/2021 | Schab .................. | B01D 15/365 |

\* cited by examiner

*Primary Examiner* — Sikarl A Witherspoon
(74) *Attorney, Agent, or Firm* — Leavitt Eldredge Law Firm

(57) ABSTRACT

A glycerin separation system heats a mixture of glycerin to about 231 degrees Fahrenheit and then allows the mixture to rest in a settling tank. Over time the mixture separates into layers of differing densities. The layers are removed individually by measuring the density of the exiting fluid. The glycerin is heating in a loop to allow for precise control of the temperature of the mixture. The pH is also controlled with a preferable level of 5.

4 Claims, 3 Drawing Sheets

GLYCERIN SEPARATION SYSTEM AND METHOD OF USE

BACKGROUND

1. Field of the Invention

The present invention relates generally to petroleum production systems, and more specifically, to a separation or refinement systems for segregating, isolating and purifying the sundry components of raw or crude oil.

2. Description of Related Art

Glycerin is traditionally produced from triglycerides or separated from a hydrocarbon source through distillation, drying or during refinement or by other complex means.

One of the problems with traditional glycerin production systems is their limited use. For example, large factories or refineries are needed to isolate the glycerin form a mixture for later use. The factories are fixed, expensive and generally not scalable.

Accordingly, although great strides have been made in the area of glycerin production systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
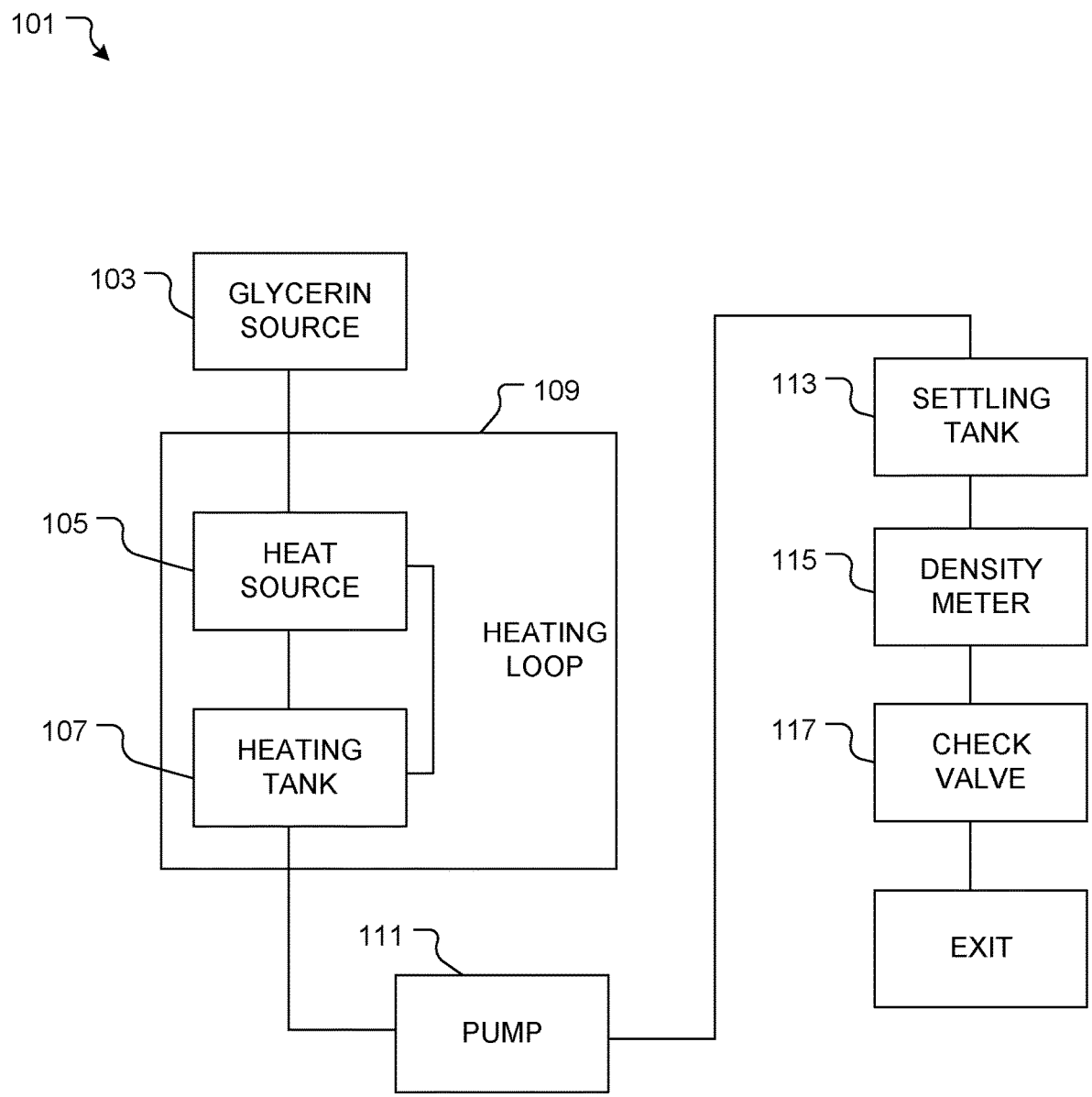
FIG. 1 is a diagram of a glycerin separation system in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional glycerin production systems. Specifically, the invention of the present application enables the simple separation of glycerin. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a diagram of a glycerin separation system in accordance with a preferred embodiment of the present application. It will be appreciated that system 101 overcomes one or more of the above-listed problems commonly associated with conventional glycerin production systems.

In the contemplated embodiment, system 101 includes a crude glycerin source 103 in fluid communication with a heating loop 109 having a heat source 105 and a heating tank 107. It is contemplated that the heat source 105 and heating tank 107 could be the same component in the system. The system 101 also having a pump 111 to move the glycerin 103 from the heating loop 109 to a first settling tank 113. The settling tank 113 having a densitometer 115 and check valve 117 in the exit line thereof.

In use, the glycerin is warmed to about 231 degrees Fahrenheit in the heating loop 109. The pH of the glycerin is adjusted to about 5.0 either prior to entry in the heating loop 109 or by injection upon exit therefrom. It will be understood and appreciated that the glycerin 103 could pass through the heat source 105 multiple times or a single time so long as it reaches about 231 degrees Fahrenheit. The glycerin is placed in the first settling tank 113 and allowed to rest for about 24-36 hours during the which the formation of at least 3 layers is anticipated. Each layer having a density different from the other two. The first layer is glycerin and is removed from the settling tank 113 first. When the densitometer 115 identifies a change in density the line is closed and cleaned via the check valve 117 whereupon the next layer which is a rag layer is removed and then the remaining layer which is composed of free fatty acids (FFA) is removed.

It should be appreciated that one of the unique features believed characteristic of the present application is that all three of the layers are of a purity and state to be commercial sold.

Another unique feature believed characteristic of the present application is that is able to operate as a continuous flow or as a batch process enabling the user to adjust the system to meet the demands of the raw material.

Figure 2:
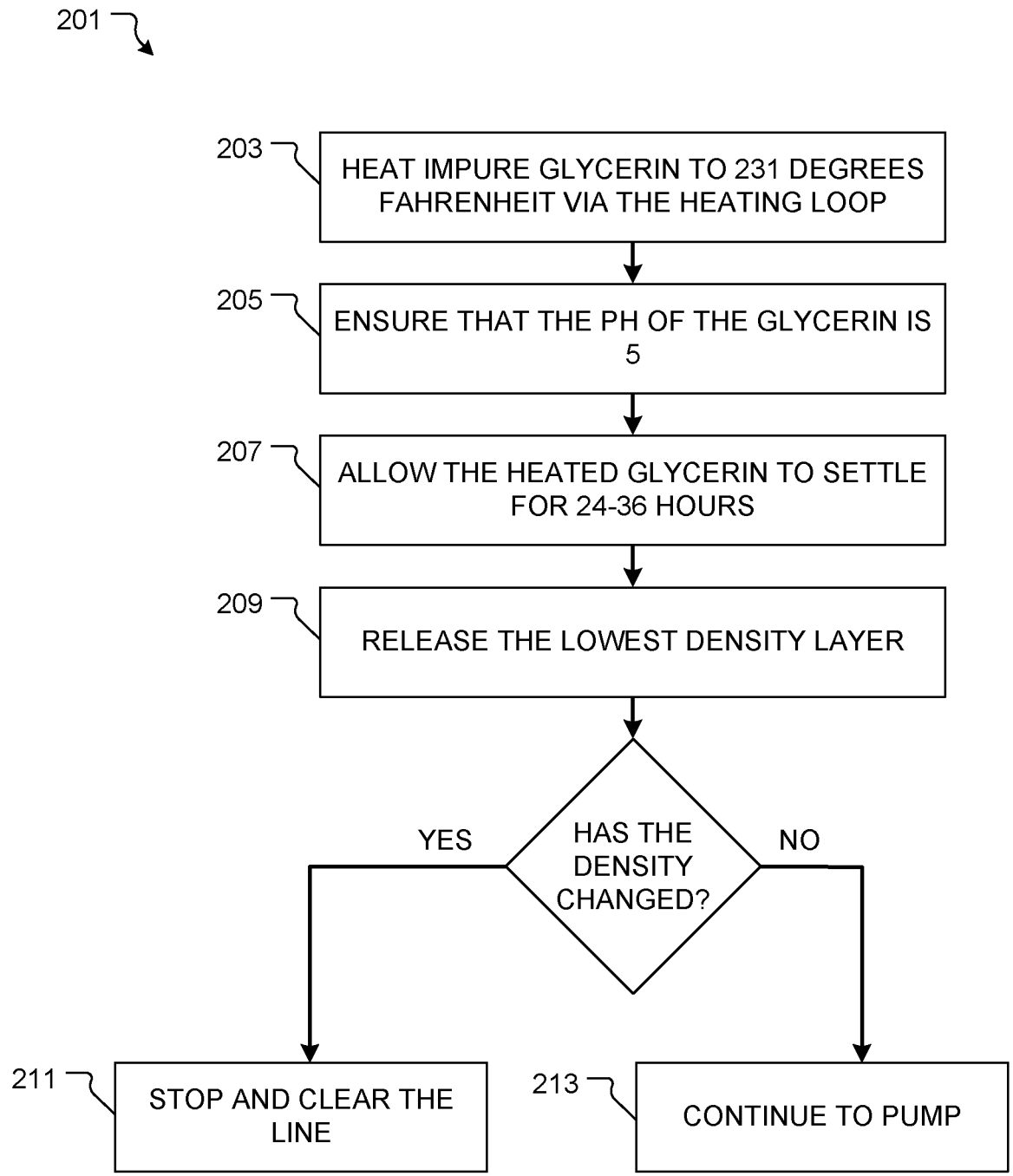
FIG. 2 is a flowchart of the preferred method of use of the system of FIG. 1.

Referring now to FIG. 2 the preferred method of use of the system is depicted. Method 201 including heating the impure or unclassified glycerin to 231 degrees Fahrenheit via the heat source and heating tank of the heating loop 203, ensuring that the pH of the glycerin is 5.0 205, allowing the heated glycerin to settle for 24-36 hours in the settling tank 207, release the lowest density layer from the settling tank 209, if the density remains the same continue to pump 213 and if the density changes stop pumping and clear the line and resume pumping 211.

Figure 3:
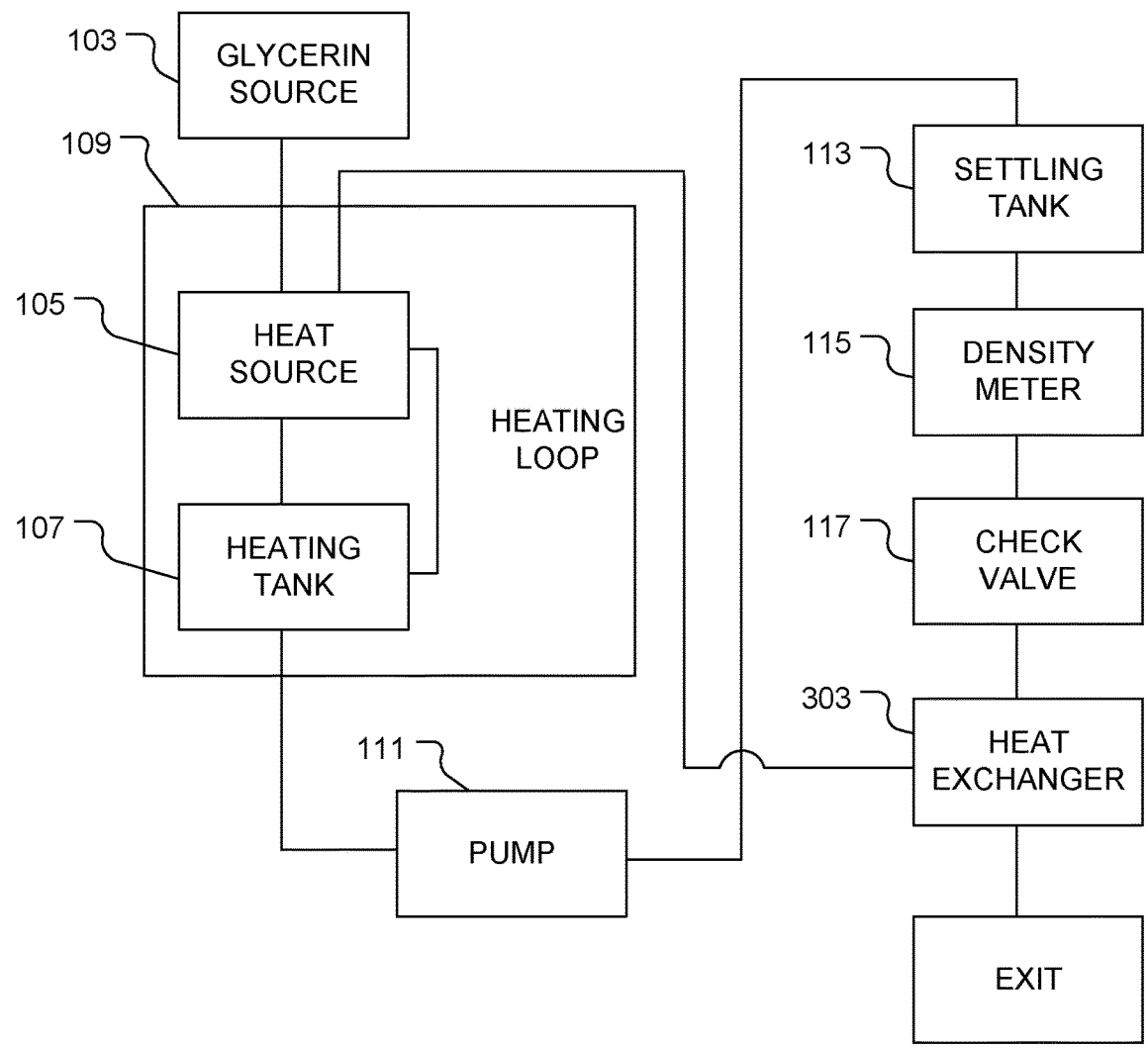
FIG. 3 is a diagram of an alternative embodiment of the system of FIG. 1.

In an alternative embodiment, as depicted by FIG. 3 where the system includes the features as previously discussed with the inclusion of a recovery heat exchanger 303 to transfer heat from the settled glycerin to the unsettled glycerin that is beginning the process. It will be appreciated that this further increases the efficiency of the system.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed:

1. A glycerin separation system comprising:
    at least one crude glycerin source in fluid communication with at least one heating loop;
        the at least one heating loop comprising at least one heat source and at least one heating tank; and
    at least one settling tank in fluid communication with the at least one heating loop, having:
        at least one densitometer; and
        at least one check valve;
    wherein the pH of the glycerin from the at least one glycerin source is altered to 5.0; and
    wherein the glycerin is removed from the settling tank.

2. The system of claim 1 wherein the temperature of the glycerin is raised to 231 degrees Fahrenheit.

3. The system of claim 1 wherein the densitometer controls the flow of fluid from the settling tank so that layers of like density material are removed individually.

4. The method of purifying glycerin given the system of claim 1, comprising:
    including heating the impure or unclassified glycerin to 231 degrees Fahrenheit via the heat source and heating tank of the heating loop;
    ensuring that the pH of the glycerin is 5.0;
    allowing the heated glycerin to settle for 24-36 hours in the settling tank;
    release the lowest density layer from the settling tank;
    if the density remains the same continue to pump; and
    if the density changes stop pumping and clear the line and resume pumping.

* * * * *